US010919967B2

(12) United States Patent
Zirlik et al.

(10) Patent No.: US 10,919,967 B2
(45) Date of Patent: Feb. 16, 2021

(54) ANTIBODIES AGAINST MAC-1

(71) Applicants: Albert-Ludwigs-Universität Freiburg, Freiburg (DE); Baker IDI Heart & Diabetes Institute Holdings Ltd., Melbourne (AU)

(72) Inventors: Andreas Zirlik, Freiburg (DE); Dennis Wolf, Schopfheim (DE); Karlheinz Peter, Hawthorn East (AU)

(73) Assignees: ALBERT-LUDWIGS-UNIVERSITÄTFREIBURG, Freiburg (DE); BAKER IDI HEART & DIABETES INSTITUTE HOLDINGS LTD., Melbourne (AU)

(*) Notice: Subject to any disclaimer, the term of this patent is extended or adjusted under 35 U.S.C. 154(b) by 0 days.

(21) Appl. No.: 16/312,629

(22) PCT Filed: Jun. 13, 2017

(86) PCT No.: PCT/EP2017/064339
§ 371 (c)(1),
(2) Date: Dec. 21, 2018

(87) PCT Pub. No.: WO2017/220369
PCT Pub. Date: Dec. 28, 2017

(65) Prior Publication Data
US 2019/0161550 A1 May 30, 2019

(30) Foreign Application Priority Data
Jun. 21, 2016 (EP) .................... 16175382

(51) Int. Cl.
C07K 16/00 (2006.01)
C07K 16/46 (2006.01)
C07K 16/28 (2006.01)
A61K 39/00 (2006.01)

(52) U.S. Cl.
CPC .... *C07K 16/2845* (2013.01); *A61K 2039/505* (2013.01); *C07K 2317/32* (2013.01); *C07K 2317/33* (2013.01); *C07K 2317/34* (2013.01); *C07K 2317/55* (2013.01); *C07K 2317/70* (2013.01); *C07K 2317/76* (2013.01)

(58) Field of Classification Search
None
See application file for complete search history.

(56) References Cited

U.S. PATENT DOCUMENTS
2014/0147445 A1  5/2014  Zirlik et al.

FOREIGN PATENT DOCUMENTS
EP  2 444 101 A1  4/2012
EP  2629787 B1 * 10/2018 ........... C07K 16/241

OTHER PUBLICATIONS

Zirlik et al. CD40 Ligand Mediates Inflammation Independently of CD40 by Interaction With Mac-1. Circulation. 2007;115:1571-1580. (Year: 2007).*
Okwor et al. Interaction of Macrophage Antigen 1 and CD40 Ligand Leads to IL-12 Production and Resistance in CD40-Deficient Mice Infected with Leishmania major. The Journal of Immunology, 2015, 195: 3218-3226. (Year: 2015).*
Altieri et al. A unique recognition site mediates the interaction of fibrinogen with leukocyte mac-1 (CD11b/CD18) . JBC 265(21) 12119-12122, 1990. (Year: 1990).*
PCT/EP2017/064339—International Search Report, dated Aug. 30, 2017.
PCT/EP2017/064339—International Written Opinion, dated Aug. 30, 2017.
Hermann Blankenbach, "Generierung und Charakterisierung eines neuen Liganden-und Akivitats-spezifischen Antikorpers zur Selektiven Hemmung der CD40L/Mac-1 Interaktion", Jun. 27, 2016.
D. Wolf, et al., "Binding of CD40L to Mac-1's I-Domain Involves the EQLKKSKTL Motif and Mediates Leukocyte Recruitment and Atherosclerosis-But Does Not Affect Immunity and Thrombosis in Mice" Circulation Research, vol. 109, No. 11, Nov. 11, 2011, pp. 1269-1279.

* cited by examiner

*Primary Examiner* — Maher M Haddad
(74) *Attorney, Agent, or Firm* — Curatolo Sidoti Co., LPA; Salvatore A. Sidoti; Floyd Trillis, III

(57) ABSTRACT

The present invention provides an isolated monoclonal antibody or an antigen-binding portion thereof which
a) binds to Mac-1,
b) specifically inhibits the interaction of CD40L with activated Mac-1 and
c) does not induce integrin outside-in signaling.

Figure 1:
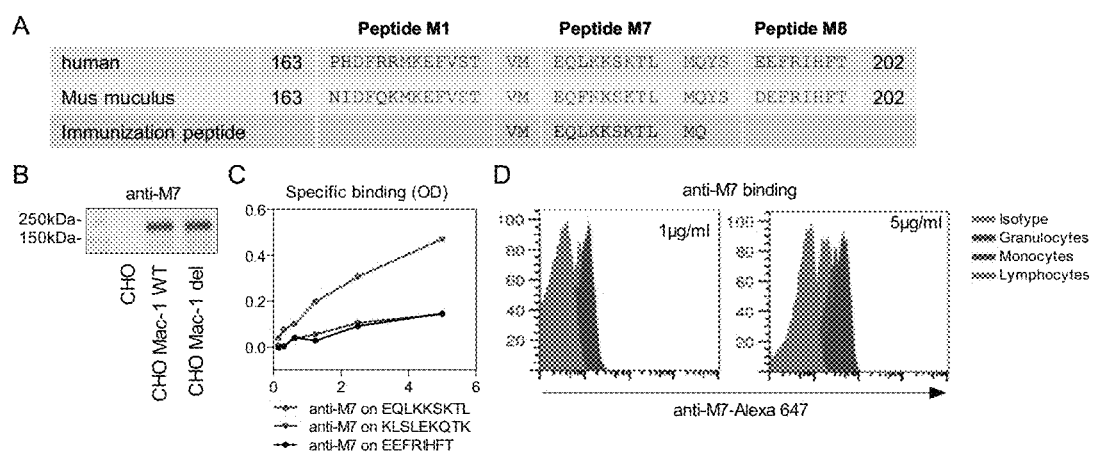

11 Claims, 9 Drawing Sheets
(8 of 9 Drawing Sheet(s) Filed in Color)
Specification includes a Sequence Listing.

SEQUENCE LISTING

```
<160> NUMBER OF SEQ ID NOS: 17

<210> SEQ ID NO 1
<211> LENGTH: 107
<212> TYPE: PRT
<213> ORGANISM: artificial sequence
<220> FEATURE:
<223> OTHER INFORMATION: light chain

<400> SEQUENCE: 1

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp His Gln Gln Lys Pro Asp Gly Thr Ile Lys Arg Leu Leu
        35                  40                  45

Tyr Ser Thr Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ile Ser Pro Pro
                85                  90                  95

Thr Phe Gly Gly Gly Thr Lys Leu Glu Ile Lys
            100                 105

<210> SEQ ID NO 2
<211> LENGTH: 6
<212> TYPE: PRT
<213> ORGANISM: artificial sequence
<220> FEATURE:
<223> OTHER INFORMATION: CDR 1

<400> SEQUENCE: 2

Gln Glu Ile Ser Gly Tyr
1               5

<210> SEQ ID NO 3
<211> LENGTH: 3
<212> TYPE: PRT
<213> ORGANISM: artificial sequence
<220> FEATURE:
<223> OTHER INFORMATION: CDR 2

<400> SEQUENCE: 3

Ser Thr Ser
1

<210> SEQ ID NO 4
<211> LENGTH: 9
```

```
<212> TYPE: PRT
<213> ORGANISM: artificial sequence
<220> FEATURE:
<223> OTHER INFORMATION: CDR 3

<400> SEQUENCE: 4

Leu Gln Tyr Ala Ile Ser Pro Pro Thr
1               5

<210> SEQ ID NO 5
<211> LENGTH: 121
<212> TYPE: PRT
<213> ORGANISM: artificial sequence
<220> FEATURE:
<223> OTHER INFORMATION: heavy chain

<400> SEQUENCE: 5

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Thr Asp Thr Ala Thr Tyr Tyr
                85                  90                  95

Cys Ala Leu Asn Tyr Tyr Asn Ser Thr Tyr Asn Phe Asp Phe Trp Gly
            100                 105                 110

Gln Gly Thr Thr Leu Thr Val Ser Ser
        115                 120

<210> SEQ ID NO 6
<211> LENGTH: 10
<212> TYPE: PRT
<213> ORGANISM: artificial sequence
<220> FEATURE:
<223> OTHER INFORMATION: CDR1

<400> SEQUENCE: 6

Gly Phe Ser Leu Ser Thr Ser Gly Met Gly
1               5                   10

<210> SEQ ID NO 7
<211> LENGTH: 7
<212> TYPE: PRT
<213> ORGANISM: artificial sequence
<220> FEATURE:
<223> OTHER INFORMATION: CDR 2

<400> SEQUENCE: 7

Ile Tyr Trp Asp Asp Lys
1               5

<210> SEQ ID NO 8
<211> LENGTH: 13
<212> TYPE: PRT
<213> ORGANISM: artificial sequence
<220> FEATURE:
<223> OTHER INFORMATION: CDR 3

<400> SEQUENCE: 8
```

```
Ala Leu Asn Tyr Tyr Asn Ser Thr Tyr Asn Phe Asp Phe
1               5                   10

<210> SEQ ID NO 9
<211> LENGTH: 9
<212> TYPE: PRT
<213> ORGANISM: artificial sequence
<220> FEATURE:
<223> OTHER INFORMATION: peptide

<400> SEQUENCE: 9

Glu Gln Leu Lys Lys Ser Lys Thr Leu
1               5

<210> SEQ ID NO 10
<211> LENGTH: 9
<212> TYPE: PRT
<213> ORGANISM: artificial sequence
<220> FEATURE:
<223> OTHER INFORMATION: peptide M7

<400> SEQUENCE: 10

Glu Gln Phe Lys Lys Ser Lys Thr Leu
1               5

<210> SEQ ID NO 11
<211> LENGTH: 13
<212> TYPE: PRT
<213> ORGANISM: artificial sequence
<220> FEATURE:
<223> OTHER INFORMATION: binding peptide

<400> SEQUENCE: 11

Val Met Glu Gln Leu Lys Lys Ala Lys Thr Leu Met Gln
1               5                   10

<210> SEQ ID NO 12
<211> LENGTH: 9
<212> TYPE: PRT
<213> ORGANISM: artificial sequence
<220> FEATURE:
<223> OTHER INFORMATION: peptide

<400> SEQUENCE: 12

Lys Leu Ser Leu Glu Lys Gln Thr Lys
1               5

<210> SEQ ID NO 13
<211> LENGTH: 8
<212> TYPE: PRT
<213> ORGANISM: artificial sequence
<220> FEATURE:
<223> OTHER INFORMATION: peptide

<400> SEQUENCE: 13

Glu Glu Phe Arg Ile His Phe Thr
1               5

<210> SEQ ID NO 14
<211> LENGTH: 13
<212> TYPE: PRT
<213> ORGANISM: artificial sequence
<220> FEATURE:
<223> OTHER INFORMATION: peptide M1

<400> SEQUENCE: 14
```

```
Pro His Asp Phe Arg Arg Met Lys Glu Phe Val Ser Thr
1               5                   10
```

```
<210> SEQ ID NO 15
<211> LENGTH: 13
<212> TYPE: PRT
<213> ORGANISM: artificial sequence
<220> FEATURE:
<223> OTHER INFORMATION: peptide M1

<400> SEQUENCE: 15

Asn Ile Asp Phe Gln Lys Met Lys Glu Phe Val Ser Thr
1               5                   10

<210> SEQ ID NO 16
<211> LENGTH: 8
<212> TYPE: PRT
<213> ORGANISM: artificial sequence
<220> FEATURE:
<223> OTHER INFORMATION: peptide M8

<400> SEQUENCE: 16

Asp Glu Phe Arg Ile His Phe Thr
1               5

<210> SEQ ID NO 17
<211> LENGTH: 13
<212> TYPE: PRT
<213> ORGANISM: artificial sequence
<220> FEATURE:
<223> OTHER INFORMATION: peptide

<400> SEQUENCE: 17

Val Met Glu Gln Leu Lys Lys Ser Lys Thr Leu Phe Ser
1               5                   10
```

ANTIBODIES AGAINST MAC-1

CROSS REFERENCE TO RELATED APPLICATIONS

This application is a national stage application of International Application No. PCT/EP2017/064339, filed 13 Jun. 2017, which claims priority from European Patent Application No. 16175382.7, filed 21 Jun. 2016, which applications are incorporated herein by reference.

In the past decades inflammation was identified as driving force of many pathologies, including atherosclerosis, Type 2 Diabetes, sepsis, myocardial infarction, autoimmune diseases and neurodegenerative disease. Targeting the inflammatory response has been proposed as major goal in these pathologies. However, a major limitation of such strategies remains that the inflammatory response is critical for regeneration, survival, and host defense. A safe and reliable anti-inflammatory therapy therefore represents a major medical need. This is illustrated by glucocorticoids, potent inhibitors of inflammation that compromise the immune response, or COX-2 inhibitors, which can suppress inflammation, but exhibit detrimental effects on the cardiovascular system.

Inflammation is a process that involves recruitment of leukocytes to the site of injury mediated by leukocyte integrins, such as Mac-1 ($\alpha_M\beta_2$, CD11b/CD18). Mac-1 is a potent adhesion factor, susceptible to rapid inflammatory activation by conformational change that exhibits increased affinity to its ligands resulting in rolling, firm adhesion, and transmigration of leukocytes into inflamed tissue. Mac-1 is a powerful target in cardiovascular disease and therapeutic or genetic inhibition of the integrin and has been shown to be highly effective in preventing atherosclerosis, neo-intima formation, and thrombotic glomerulonephritis. Besides its role in inflammation, Mac-1 was initially named CR (complement receptor) 3 by its ability to bind complement factors, such as C3bi, reflecting its role in host defense, wound healing, thrombosis, and various other myeloid cell effector functions. This broad repertoire of effector functions is realized by a broad expression on the myeloid lineage, including on monocytes, macrophages, and neutrophils, but also on NK cells, and to a smaller extent on activated lymphocytes. Its functional diversity is furthermore reflected by promiscuous ligand binding to a large repertoire of proteins and proteoglycans, including ICAM-1, fibrinogen, fibronectin, heparin, GPIbα, RAGE, endothelial protein C-receptor (EPCR), and CD40L. It has been proposed that integrin antagonism is a promising target in inflammation. However, its role in host defense and thrombosis may limit its clinical use.

CD40 ligand (CD40L) is a transmembrane molecule of crucial interest in cell signaling in innate and adaptive immunity. It is expressed by a variety of cells, but mainly by activated T-lymphocytes and platelets. CD40L may be cleaved into a soluble form (sCD40L) that has a cytokine-like activity. Both forms bind to several receptors, including CD40. This interaction is necessary for the antigen specific immune response. CD40L binds also to different receptors whereby Mac-1 (αMβ2) is one receptor whereby said interaction plays a role in arterial neo-intima formation, leukocyte recruitment and atherosclerosis, pathogenesis of atherothrombosis, monocyte adhesion and neutrophil infiltration and release of pro-inflammatory cytokines (IL-8, IL-6).

Mac-1 is a classical adhesion factor involved in a variety of inflammatory pathologies. Despite its promoting effect on leukocyte recruitment in atherosclerosis and peritoneal inflammation, Mac-1 targeted therapy is limited by various side effects, such as impaired wound healing and host defense. This is further reflected by the human Leukocyte Adhesion Deficiency (LAD), which is characterized by a defect of the integrin Mac-1, LFA-1, and CD11c in the β-subunit that impairs host defense. Unspecific attempts to therapeutically inhibit Mac-1 seem therefore not favorable. To circumvent these limitations novel monoclonal antibodies are provided that specifically target the binding of CD40L to Mac-1's major ligand binding I-domain within the am-subunit of the integrin. CD40L represents a biased agonist for Mac-1, mediating its pro-inflammatory function by serving as endothelial adhesion factor for CD40L, but not by activation of outside-in signaling pathways. CD40L/Mac-1 binding does not interfere with CD40L-CD40 or Mac-1-GP1balpha and Mac-1-ICAM-1 binding, suggesting unique binding epitopes on each of the protein surfaces.

Integrins are major adhesion receptors that transmit signals bidirectionally across the plasma membrane, playing significant roles in diverse biological processes including immune response. Integrins contain two non-covalently associated type 1 transmembrane glycoprotein α and β subunits; each subunit contains large extracellular domains, a single-spanning transmembrane domain and short cytoplasmic domain. The ability of the integrin's extracellular domain to bind ligands depends on an open-extended confirmation of the αM subunit ("activation") and regulates cell adhesion and signal transduction, both outside-in and inside-out signaling. The present invention relates to a specific modification of the interaction between CD40L and the integrin $\alpha_M\beta_2$ (Mac-1).

It has been found that inactivation of distinct integrin functions involved in inflammatory, but not in regenerative or immune pathways could be achieved by selectively blocking Mac-1's interaction to specific ligands, while not affecting others.

Monoclonal antibodies, specifically targeting the EQLKKSKTL (SEQ ID NO:9) binding motif in Mac-1, which we have demonstrated to be required for binding to its adhesive, pro-inflammatory ligand CD40L have been constructed.

The present invention provides therefore isolated monoclonal antibodies or antigen-binding portions thereof, which inhibit the recruitment of leukocytes without undesired side effects. Such antibodies or antigen-binding portions thereof
  a) bind to Mac-1,
  b) specifically inhibit the interaction of CD40L with activated Mac-1, and
  c) do not induce integrin outside-in signaling.

In the course of the present invention monoclonal antibodies have been constructed whereby the most preferred embodiment is the antibody in the following designated as anti-M7. The sequence of the antibody has been determined and the CDRs were identified. With this information and computational and conventional binding studies it is possible to provide suitable other antibodies or antigen-binding fragments thereof, which are derived from this antibody. Since antibody technology has gained much interest in the therapeutic area there are several engineered antibody fragments available which can be used in practice. The term "monoclonal antibody or antigen-binding fragment thereof" is understood in a broad sense and includes therefore not only the $F_{ab}$ fragments but also single-chained Fv fragments (scFv), diabodies which may be bispecific, bispecific single chain fragments, triabodies, tetrabodies or minibodies. The sequence information provided herein can also be used to produce nanobodies which are derived from camelite immunoglobulins. Many of those structures are summarized in the review article of Holliger et al. (Nature Biotechnology, vol. 23, no. 9 (2005), pp 1126-1136).

It is a preferred property of the isolated monoclonal antibodies or antigen-binding portions thereof that they bind to Mac-1, whereby, however, the binding to the activated Mac-1 is preferred whereas the antibody structures of the present invention should not bind to non-activated Mac-1. A distinction between activated and non-activated Mac-1 can be performed by quantifying the binding kinetics as for example described by Li et al. (Journal of Immunology (2013), pp 4371-4381).

Another preferred embodiment of the isolated monoclonal antibodies or antigen-binding portions thereof of the present invention is that they limit the expression of inflammatory cytokines.

Another preferred property of the isolated monoclonal antibodies or antigen-binding portions thereof is that they block leukocyte recruitment in vitro and preferably in vivo. Such blockage can be observed and measured in intravital microscopy as shown in the examples of the present application.

A further preferred embodiment of the monoclonal antibodies or antigen-binding portions thereof is that the thrombotic and hemostatic functions of Mac-1 are not effected. This can be measured by using suitable in vivo experiments.

The preferred embodiment disclosed herein designated as anti-M7 was produced as a monoclonal antibody in the mouse system. It is well-known to the skilled person that monoclonal murine antibodies cannot be used in the therapy of humans since after repeated administration of such murine antibodies anti-mouse antibodies are generated in the patient. Therefore, the monoclonal antibodies or antigen-binding portions thereof are preferably humanized. Humanization means that the mouse framework of the antibody is replaced by a human framework structure of an antibody which has high similarity to the mouse antibody. By using suitable computational models further adaptations of the amino acid structure can be made in order to reduce the mouse character of the antibody. It has, however, to be checked whether the proposed changes in the amino acid sequence reduce the binding strength of the humanized antibody or antigen-binding construct. Only such amino acid substitutions are performed which do not negatively affect the binding properties and in particular the specificity.

It is assumed that such modified antibodies or antigen-binding portions thereof should comprise at least three CDRs. The CDRs are disclosed and have SEQ ID NOs:2-4 and 6-8, respectively. In a more preferred embodiment the monoclonal antibodies or antigen-binding portions thereof according to the present invention comprise at least four, more preferred five and in particular preferred six CDRs having the sequences of SEQ ID NOs:2-4 and 6-8, respectively.

The light chain of the anti-M7 antibody has the amino acid sequence as provided in SEQ ID NO:1 and the heavy chain corresponds to SEQ ID NO:5. As already explained above, in the course of humanization amino acid sequence changes are introduced into the amino acid sequence. In preferred embodiments the isolated monoclonal antibodies or antigen-binding portions of the present invention have a light chain which has an amino acid identity of at least 80%, preferred of at least 85%, more preferred of at least 90% and in particular preferred of at least 95% identity to SEQ ID NO:1.

In preferred embodiments the isolated monoclonal antibodies or antigen-binding portions of the present invention have a heavy chain which has an amino acid identity of at least 80%, preferred of at least 85%, more preferred of at least 90% and in particular preferred of at least 95% identity to SEQ ID NO:5.

The term "identity" means that the sequence of the original murine sequence and the sequence of the humanized construct are compared to each other. An identity of for example 90% means that 90% of the amino acids are at the corresponding amino positions identical in the original mouse sequence and in the humanized sequence.

The isolated monoclonal antibodies or antigen-binding portions thereof of the present invention can preferably be used in pharmaceutical compositions which comprise a pharmaceutically active amount of the antibody or antigen-binding portion thereof together with additives suitable for the application to a patient whereby intraperitoneal application is especially preferred. The pharmaceutical compositions of the present invention can preferably be used for the inhibition of inflammation.

It turned out that the monoclonal antibodies or antigen-binding portions thereof according to the present invention can preferably be used in the treatment of inflammatory complications following myocardial infarction. In such complications, which occur frequently after myocardial infarction inflammatory leukocytes attracted to the area which is affected by the myocardial infarction cause and contribute to an inflammatory response that aggravates wound healing and may inhibit the recovery after myocardial infarction. In such embodiments the antibodies and antigen-binding portions thereof according to the present invention are preferably used.

The inhibition of inflammation by anti-M7 or the derivatives derived therefrom provides several advantages over a conventional anti-Mac-1 therapy. It has been observed that mice treated with formerly known anti-Mac-1 antibodies showed increased mortality compared to control mice. These data confirm previous studies in which Mac-1 deficient mice were not protected from bacterial sepsis, an effect most likely caused by the inability to bind complement factors and promote clearance of bacterial particles e.g. by C3bi-mediated phagocytosis.

Previous epitope mapping studies have revealed and located the binding of C3bi to the residues $P^{147}$-$R^{152}$, $R^{201}$-$K^{217}$, and $K^{245}$-$R^{261}$ within the $\alpha_M$ I-domain, demonstrating a binding epitope that is distinct from the binding sequence required for CD40L ($E^{162}$-$L^{170}$). It has been shown that mice treated with anti-M7 show increased survival compared to anti-Mac-1 and IgG-control treated mice, indicating that anti-M7 does not only lack detrimental properties, but induces protective effects.

It is assumed that suppression of pro-inflammatory leukocyte adhesion in the peritoneum helps to slow-down the overwhelming pro-inflammatory response accompanying the initial attempt to remove and fight the bacterial invasion. It is recognized that the balance between protective and disease aggravating pathways is disturbed in many conditions and might potentially been shifted to the protective side by limiting leukocyte recruitment. This hypothesis is further supported by the fact that anti-M7 protected from pro-inflammatory cytokine levels in plasma compared with control animals, while anti-Mac-1 raised cytokine levels. Thus, the reduction in cytokine levels may be secondary to diminished leukocyte activation and activation in target tissues. Indeed, intimal mononuclear cells produce pro-inflammatory cytokines, such as TNFα, IL-1, IFNγ as well as anti-inflammatory mediators IL-10. In plasma, mice challenged with TNFα and treated with anti-M7 antibody showed a reduction of the pro-inflammatory cytokines IL-6, TNFα and MCP-1, while anti-Mac-1 induced enhanced cytokine expression.

However, treatment with other anti-Mac-1 antibodies, such as the clone M1/70 (which is used as control), might not entirely reflect the genetic knock-out. It is noteworthy to mention that M1/70 induces a strong pro-inflammatory response in Mac-1 expressing cells, in particular in macrophages, and elevates cytokine expression. The latter is also confirmed by our results, demonstrating that a single injection of anti-Mac-1 results in strongly up-regulated cytokine plasma levels, likely affecting wound healing. It has been suggested that over-stimulation as provided by M1/70 could represent a feasible strategy to resolve inflammation by activation of apoptotic pathways. Indeed, it has previously been shown that apoptosis of cells resident in the peritoneal cavity was enhanced after a single injection of anti-Mac-1 clone M1/70. This could potently support anti-Mac-1's effect in decreasing peritoneal cell accumulation. However, an apoptosis inducing therapy, accompanied by a cytokine-storm is likely unfavorable in the clinical practice.

Mac-1 supports interaction to multiple other molecules and more are likely of not been discovered so far. More than 40 different protein interactions have been described, but molecular binding properties of only some of these is known. Therefore it is not to exclude that the binding site of CD40L is shared by other ligands as wells. However, the data presented herein unveil and confirm previous suggestions that CD40L binding to Mac-1 does not share many features with binding properties to other conventional ligands:

(1) While binding epitopes identified for fibrinogen and other ligands show overlapping regions, the EQLKKSKTL (SEQ ID NO:9) motif within Mac-1's I-domain is not involved in binding of alternative ligands,
(2) neither CD40L itself, nor anti-M7 did induce integrin outside-in signaling, while this feature of integrin physiology has been considered as paradigm in integrin ligand binding so far,
(3) CD40L's interaction with Mac-1 does not expand on immune or haemostatic function, while most of Mac-1 ligands, such as Fibrinogen, are involved in multiple of those pathologies.

The data presented herein propose that the interaction of CD40L with Mac-1 is primarily required for firm adhesion of inflammatory leukocytes, presumably of granulocytes in a variety of inflammatory pathologies. The results do not rule out, but emphasize that immune function, haemostatic parameters and regenerative response do not involve binding of CD40L to Mac-1.

It has been shown previously that treatment with the specific inhibitor of the CD40L/Mac-1 interaction, cM7, attenuates inflammatory leukocyte recruitment in a model of intravital microscopy in inflamed cremaster venules, and in a model of sterile peritonitis. It is demonstrated that treatment with either the full IgG antibody anti-M7 or $F_{ab}$ fragments thereof, directed against the CD40L binding site on Mac-1, significantly reduces leukocyte adhesion. Interestingly, the inhibitory efficiency of anti-M7 is comparable to that of anti-Mac-1 treatment, suggesting the CD40L/Mac-1 interaction as instrumental for leukocyte recruitment. This does not falsify previous reports, but does extend the repertoire of Mac-1's ligands expressed on the endothelium, ICAM-1 and RAGE, by CD40L. In this regard, it is plausible that patterns of counter-receptor binding depend on pathologies and the inflammatory burden. Thereby, it is either possible that the interaction of CD40L and Mac-1 is disease specific and regulated by either expression of endothelial CD40L, by conformational change of Mac-1 or that some pathologies are more dependent on leukocyte invasion than others. For example, atherosclerosis—a disease in which myeloid cell recruitment is needed at least in early stages of disease—was strongly susceptible to blockade of the CD40L/Mac-1 interaction, while neo-intima formation after a wire injury was not inhibited by blocking CD40L/Mac-1, but by anti-Mac-1 or in Mac-1 knock-out mice.

The data obtained in the course of the present invention show that anti-M7 was most effective in blocking the interaction to activated Mac-1, but not to non-activated Mac-1. This proposes that the interaction may play a more important role in pathologies associated with a higher inflammatory burden, rather than under baseline conditions.

Also, it remains to be answered whether an antibody such as anti-M7 can actively modulate or conserve different conformations of the integrin as previously proposed. This could explain that only the permanently-activated integrin, but not the integrin in native condition was targeted as the data show. However, for the determination of the exact binding properties a more detailed structural analyses may be helpful.

Finally, it cannot be excluded that CD40L/Mac-1 interaction may be responsible for the egress and mobilization of monocyte from the bone marrow or the spleen as previously suggested. As observed herein, inflammatory monocytosis during sepsis could be completely reversed by anti-M7 treatment. Whether this is caused by impaired monocyte reservoirs, e.g. by impaired migration to the spleen, shall be determined in further experiments.

The antibodies of the present invention follow a strategy to selectively target the EQLKKSKTL (SEQ ID NO:9) binding motif, representing CD40L's binding site within the Mac-1 I-domain, by a monoclonal antibody anti-M7. This antibody is highly selective for the targeted binding site, does not interfere with alternative binding partners, and—in contrast to conventional anti-Mac-1 antibodies—does not affect haemostasis, host defense and wound healing. In preferred embodiments the antibodies of the present invention do not interfere with alternate binding partners and are therefore highly selective for the targeted binding site. The proposed ligand-targeted anti-integrin therapy is superior to an unselective approach and represents an advantage to refine and adjust anti-integrin therapy against inflammatory disease.

The results, experiments and advantages obtainable by the present invention are summarized in the Figures and the Examples. Figures and Examples show preferred embodiments of the present invention, in particular the most preferred antibody anti-M7, but it should be understood that Figures and Examples should not be considered as limiting the present invention.

The preferred embodiments of the invention are shown in the Figures and in the Examples:

BRIEF DESCRIPTION TO DRAWINGS

The patent or application file contains at least one drawing executed in color. Copies of this patent or patent application publication with color drawing(s) will be provided by the Office upon request and payment of the necessary fee.

FIG. 1 shows that A mouse monoclonal antibody raised against the CD40L binding site within human Mac-1, anti-M7, is effective in targeting the human integrin. The peptide sequence M7 within the Mac-1, required for binding of CD40L, is a highly conserved binding motif between the human (SEQ ID NO:9) and murine (SEQ ID NO:10) integrin (FIG. 1A).

Furthermore, FIG. 1A shows the peptide M1 of human origin (SEQ ID NO:14) and the corresponding peptide M1 derived from *Mus musculus* having SEQ ID NO:15. The human peptide having the designation M8 corresponds to SEQ ID NO:13 and the peptide M8 derived from *Mus musculus* has SEQ ID NO:16.

Antibody anti-M7 generated by immunization of mice with the binding peptide VMEQLKKAKTLMQ (SEQ ID NO:11) coupled to diphtheria toxoid bound to a CHO cell line over-expressing native (WT) and permanently activated Mac-1 (del), but not to control CHO cells in western blot (FIG. 1B).

Specific binding of the antibody anti-M7 to the immobilized peptides M7 (EQLKKSKTL) (SEQ ID NO:9), sM7 (KLSLEKQTK) (SEQ ID NO:12), and M8 (EEFRIHFT) (SEQ ID NO:13) was tested in a solid phase binding with immobilized peptides (FIG. 1C).

Binding was quantified by binding of biotinylated anti-mouse IgG and color reaction after incubation with HRP-coupled streptavidin. Specific binding was calculated by subtraction of binding of mouse IgG to the peptides. Anti-M7 was coupled with the fluorochrome Alexa647 and binding to human leukocyte subsets was quantified in FACS. Alexa647 Isotype antibody served as control (FIG. 1D).

Figure 2:
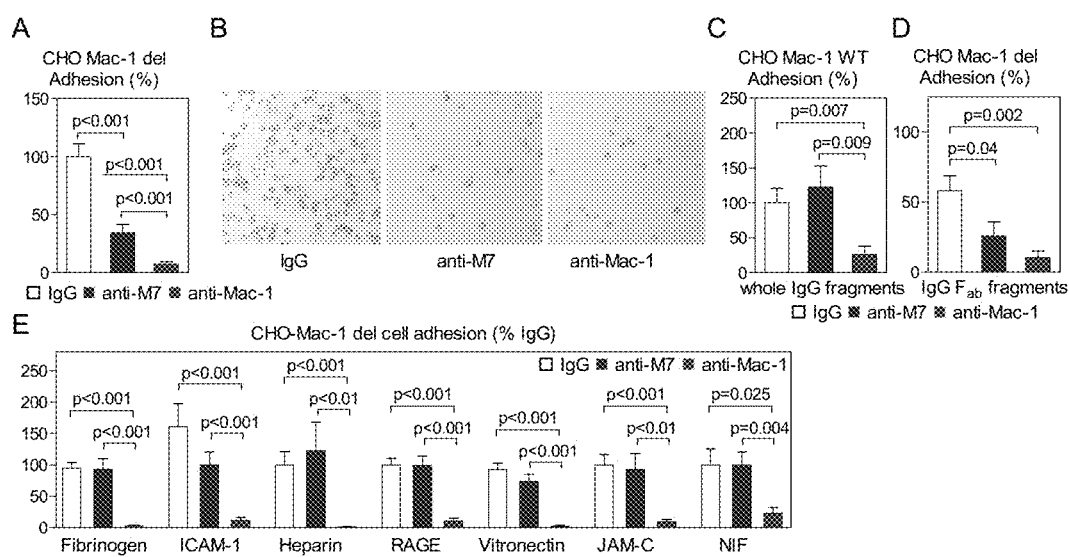

FIG. 2 shows that Anti-M7 selectively blocks the interaction of permanently activated Mac-1 with CD40L, but not of the native integrin or to alternative Mac-1 ligands. CHO-cells over-expressing the permanently activated Mac-1 mutant (Mac-1-del) adhered to immobilized CD40L in a static adhesion assay (FIG. 2A, 2B).

Cells were incubated with anti-M7 or the human pan-I-Domain blocking reference clone 2LPM19c 15 min prior to adhesion. Alternatively, adhesion of the native, non-activated Mac-1 integrin was tested (FIG. 2C). To exclude unspecific Fc-mediated interaction, $F_{ab}$-fragment preparation of anti-M7 or anti-Mac-1 were used as inhibitor (FIG. 2D).

To test whether anti-M7 is specific for CD40L, a panel of classical Mac-1 ligands were separately immobilized and adhesion of permanently activated Mac-1 CHO cells was quantified in the presence of anti-M7 or pan I-Domain blocking anti-Mac-1 (FIG. 2E).

Figure 3:
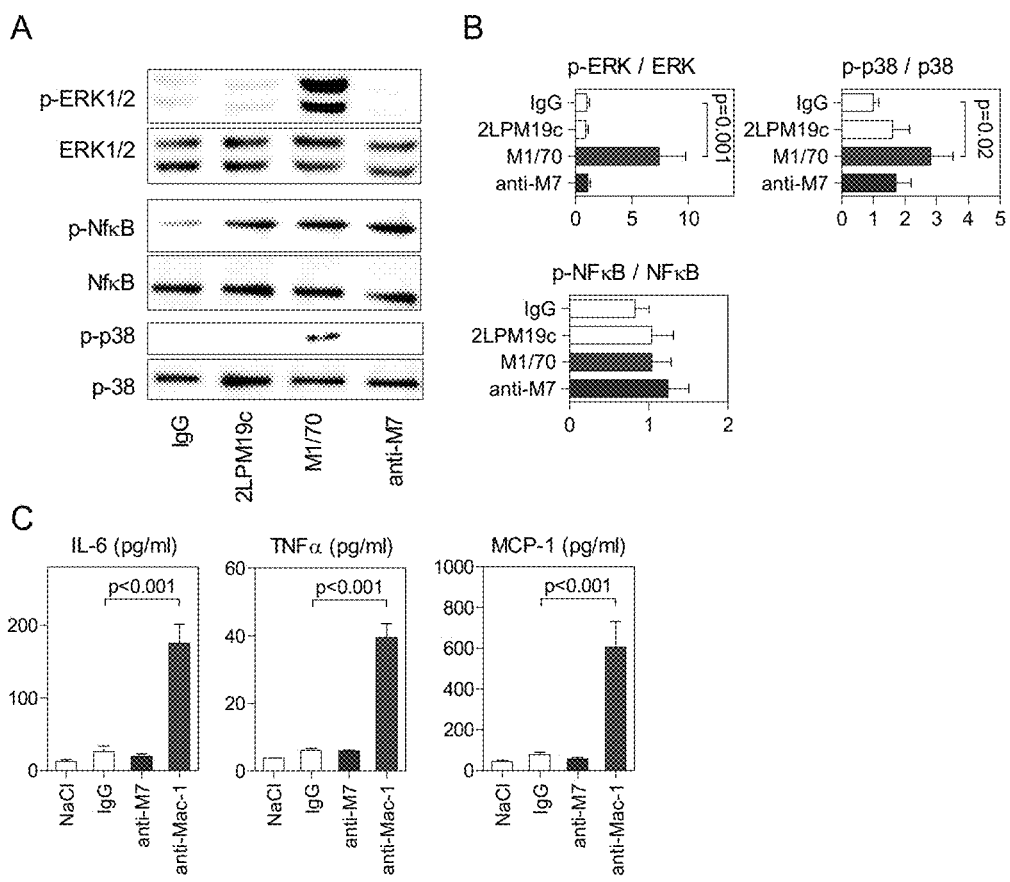

FIG. 3 shows that Anti-M7 does not induce integrin outside-in signaling, while conventional anti-Mac-1 antibodies induce activation of MAP-kinases and inflammatory cytokine expression in vitro and in vivo.

Murine macrophages were isolated by injection of 4% thioglycollate in the peritoneum of C57Bl/6 mice and incubation for 72 hours. Peritoneal cells were collected by peritoneal lavage, FACS analysis confirmed purity of >90 percent F4/80$^+$ macrophages. Macrophages were cultured in 5% FCS RPMI overnight and stimulated with 10 µg/ml of mouse IgG, anti-human Mac-1 (clone 2LPM19c), anti-mouse Mac-1 (clone M1/70) or anti-M7 for 30 min. Cells were lysed and phosphorylated ERK1/2, NfκB and p38 were visualized by western blot (FIG. 3A), and the ratio of phosphorylated fractions was calculated (FIG. 3B). Values were calculated as relative arbitrary units (AU) normalized to signal of cells stimulated with saline alone. Mac-1 antibody clones were injected i.p. in mice and serum concentration of IL-6, TNFα, and MCP-1 was measured by cytometric bead array 4 hours after injection (FIG. 3C). Anti-Mac-1 clone 1/70 was used as control.

Figure 4:
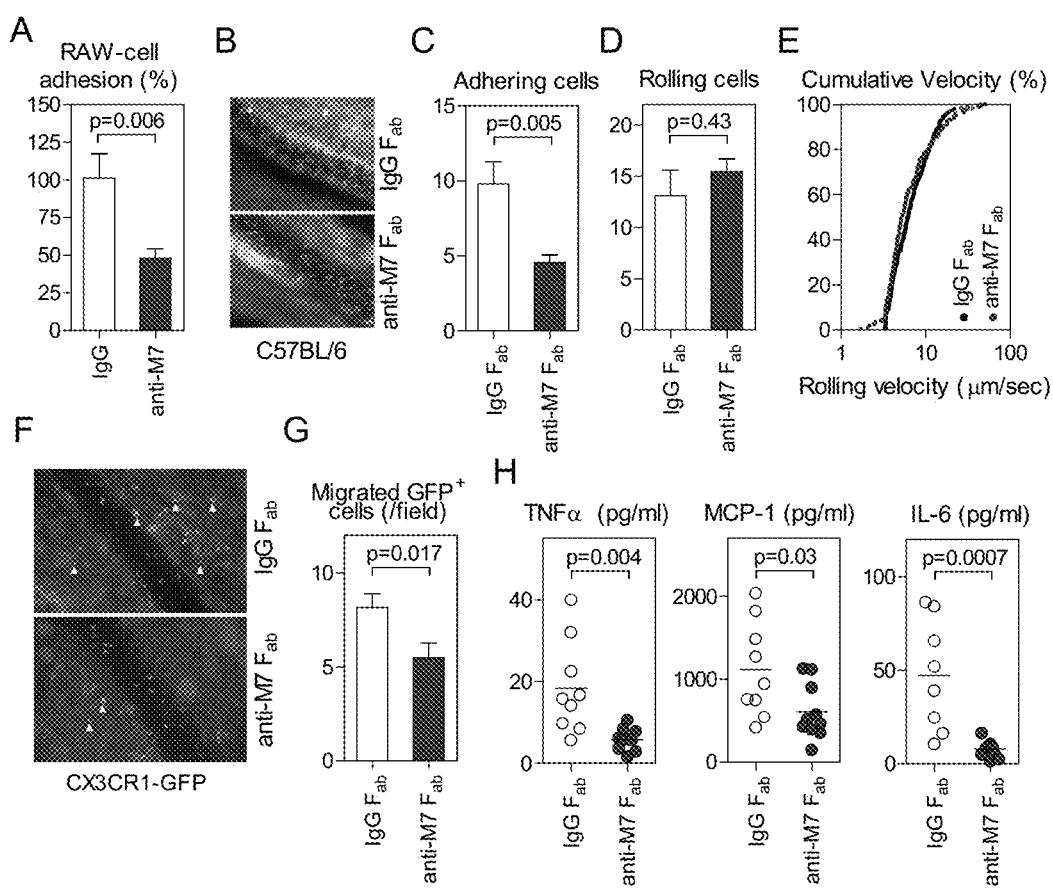

FIG. 4 shows that treatment with anti-M7 prevents inflammatory leukocyte recruitment in vitro and in vivo and decreases inflammatory cytokine expression. Murine RAW-cells were allowed to adhere on isolated and TNFα-primed murine endothelial cells in vitro in a flow chamber assay. Number of adhering cells was quantified in the presence of an anti-mouse IgG or anti-M7 antibody (FIG. 4A). C57Bl/6 mice were injected with 200 ng TNFα i.p. to induce peritoneal and mesenteric inflammation. Simultaneously, either IgG isotype control or anti-mouse anti-Mac-1 (clone M1/70) $F_{ab}$-fragment preparations were injected. Leukocyte recruitment to inflamed mesenteric venules was monitored by intravital microscopy 4 hours after injection (FIG. 4B). Number of adhering and rolling leukocytes were quantified, as well as leukocyte rolling velocity, displayed as cumulative frequency (FIG. 4C-E). Mice expressing GFP in monocytes (CX3CR1-GFP) were subjected to intravital microscopy in the presence of IgG or anti-M7 $F_{ab}$ preparations (FIG. 4F). Migrated monocytes (white arrows) were quantified in the para-vascular space in the viewing field (FIG. 4G). Plasma cytokine levels in mice subjected to intravital microscopy after IgG or anti-M7 $F_{ab}$ treatment were assessed by CBA bead array (FIG. 4H).

Figure 5:
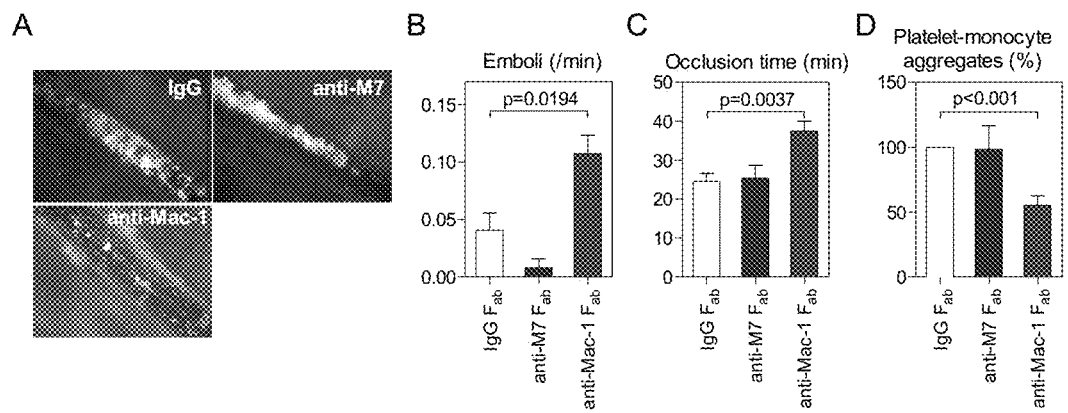

FIG. 5 shows that Anti-M7 does not affect venous thrombosis and platelet effector function in vivo. Venous thrombosis was induced in mesenteric venules of C57Bl/6 mice by ferric chloride. Thrombus formation was visualized by in vivo rhodamine staining in intravital microscopy (FIG. 5A). Time to thrombus-occlusion of the vessel and rate of emboli (/min) was monitored and quantified (FIG. 5B, 5C). Mice were treated with either $F_{ab}$-preparation of mouse IgG, anti-M7 or anti-Mac-1 (50 µg) by intraperitoneal injection 15 min prior to thrombus induction. Formation of platelet-monocyte aggregates was quantified by detection of CD41$^+$ monocytes in flow cytometry after treatment with anti-Mac-1 antibody clones (FIG. 5D).

Figure 6:
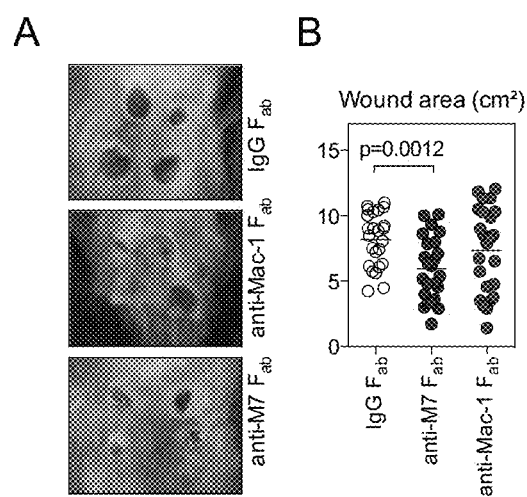

FIG. 6 shows that specific inhibition of Mac-1's interaction to CD40L, but not to other ligands, improves skin wound healing. Aseptic skin wounds were induced by a 4-mm biopsy punch after injection of anti-Mac-1 or anti-M7 $F_{ab}$ preparations. After 6 days skin wounds were photographed (FIG. 6A) and wound area was calculated (FIG. 6B).

Figure 7:
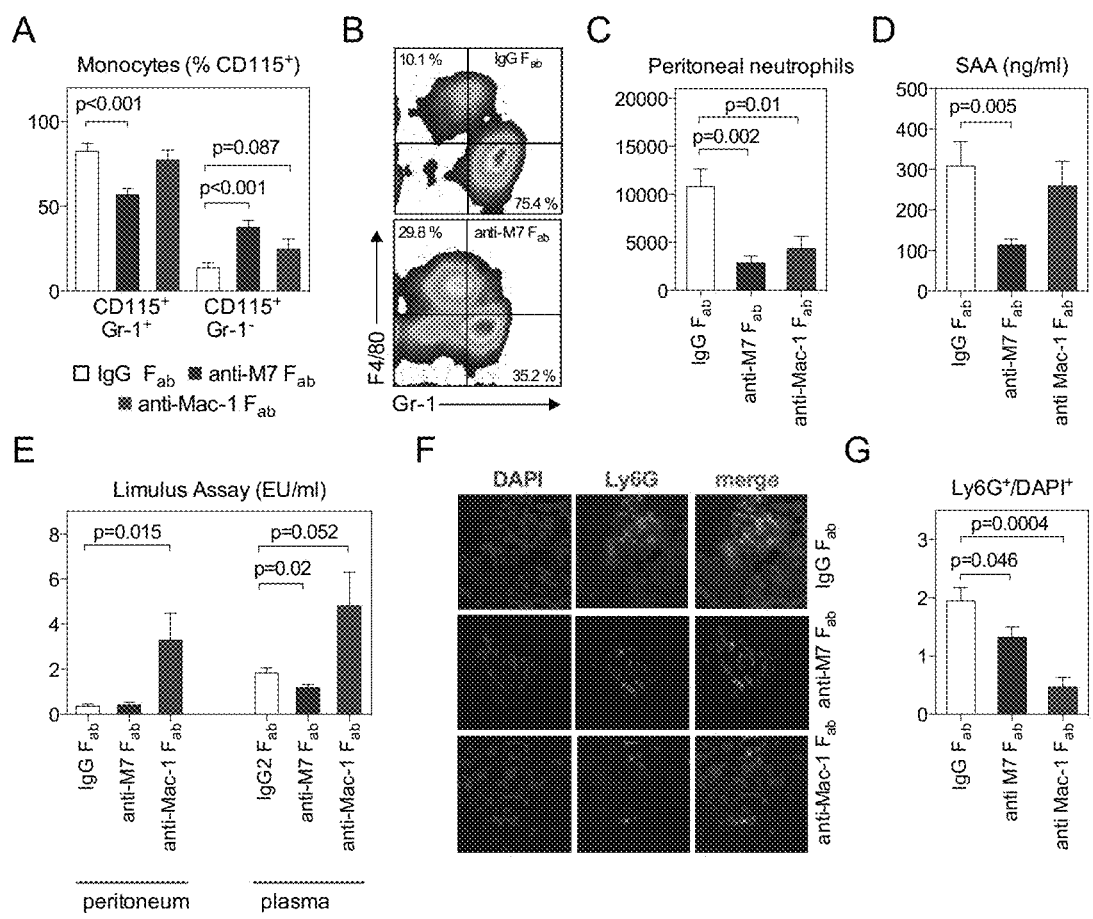

FIG. 7 shows that Anti-M7 improves host defense, bacterial clearance, and inflammation during bacterial sepsis, while unspecific blockade of Mac-1 potentiates bacteremia in mice. To test whether blockade of Mac-1 or specifically of the CD40L binding site affects host defense and inflammation during bacterial sepsis, coecal-ligation and puncture sepsis (CLP) was induced. 20 hours after CLP procedure inflammatory and patrolling monocytes circulating in blood were quantified by flow cytometry (FIG. 7A). Granulocytes (F4/80$^-$Gr-1$^+$) invading into the peritoneal cavity were identified by flow cytometry (FIG. 7B) and total numbers were calculated (FIG. 7C). Levels of the acute phase protein SAA (FIG. 7D) and of bacterial LPS titers (FIG. 7E) were quantified in plasma. Accumulation of granulocytes in kidney parenchyma was determined by staining against DAP and Ly6G (FIG. 7F) and quantified as ratio of granulocytes/total cell nuclei (FIG. 7G).

Figure 8:
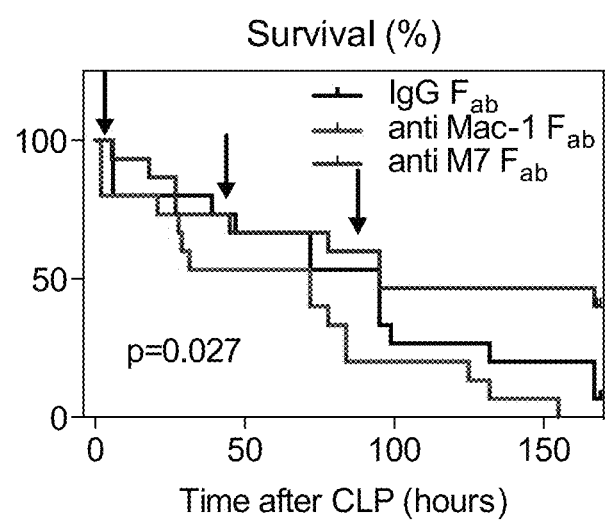

FIG. 8 shows that Anti-M7 improves, while anti-Mac-1 decreases, survival during CLP-sepsis. Coecal-ligation and puncture sepsis (CLP) was induced. To assess if treatment with Mac-1 antibody clones affects survival, mice were treated by intraperitoneal injection with either anti-Mac-1 or anti-M7 $F_{ab}$ preparations at 0, 48, and 96 hours after induction of CLP sepsis. Relative survival was calculated and displayed as Kaplan-Maier survival cure.

Figure 9:
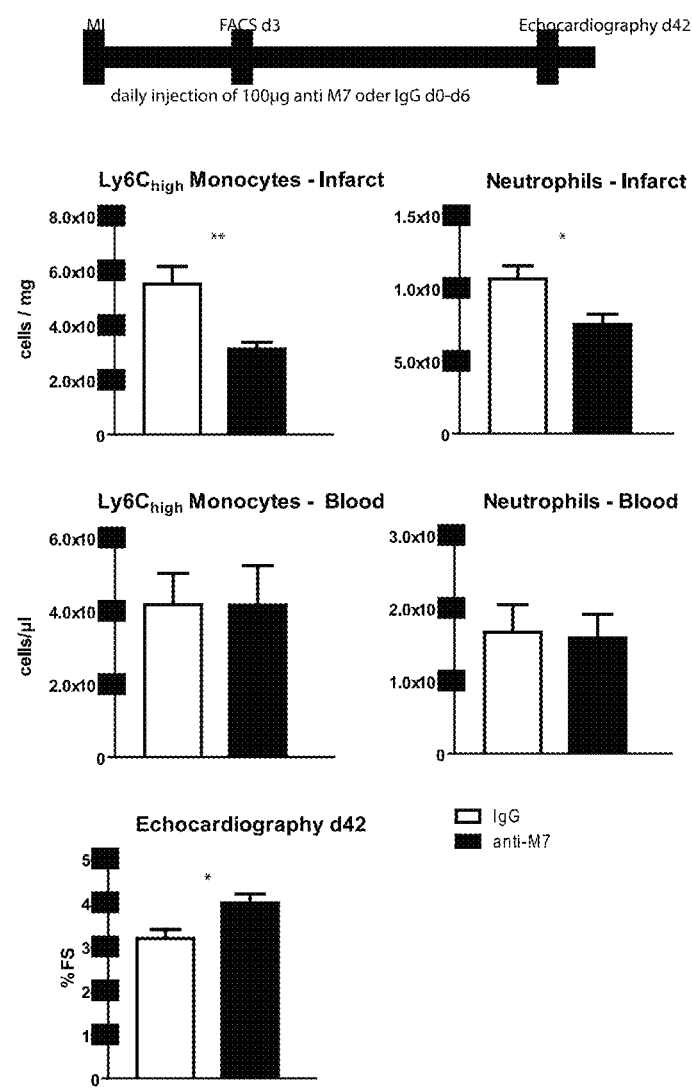

FIG. 9 shows that treatment with Anti-M7 blocks inflammatory leukocyte infiltration in the injured myocardium following myocardial infarction. Myocardial infarction was induced by a surgical ligation of the left anterior descending coronary artery (LAD). Leukocytes infiltrating the infarcted myocardium were quantified by flow cytometry in digested hearts after myocardial infarction. Anti-M7 decreased the infiltration with monocytes and neutrophils and attenuated heart failure as assessed by echocardiography.

The results summarized in the Figure were obtained in the following examples:

EXAMPLE 1

Male mice on a C57BL/6N background received a standard chow diet. All mice were maintained under standardized conditions (12-hour light, 12-hour dark cycle) and had access to food and water ad libidum. At the age of 8 weeks, mice were subjected to intravital microscopy, wound healing or CLP sepsis as indicated. Treatment with antibodies was performed by intraperitoneal injection in the indicated concentration at a volume of 100 uL per injection. In some intravital experiments, GFP-transgene animals under the control of CXCR3-promoter (CXCR3-GFP) were used to track leukocytes. All experimental protocols were approved by the animal ethics committee of the Alfred Medical Research and Education Precinct (AMREP), Melbourne, Australia and the local animal ethics committee at the University of Freiburg. All procedures were carried out in accordance with institutional guidelines.

An antibody specific for a peptide corresponding to Mac-1 I-domain sequence V160-S172 was obtained by immunizing mice with the peptide C-VMEQLKKSKTLFS-NH2 (SEQ ID NO:17) coupled to diphtheria toxoid (Monash Antibody Technologies Facility, Monash University, Melbourne, Australia). Solid phase binding assays was employed to screen binding of sera to the immobilized peptide M7. Among different clones binding with high affinity to M7, the preferred clone RC3 (termed anti-M7) was further characterized.

EXAMPLE 2

A mouse monoclonal antibody raised against the CD40L binding site within human Mac-1, anti-M7, is effective in targeting the human integrin.

It has previously been shown that CD40L selectively binds to the EQLKKSKTL (SEQ ID NO:9) motif within the major Mac-1 ligand-binding domain. To obtain a specific inhibitor of the human binding site, mice were immunized with the human peptide V160-S172 containing the binding peptide M7. Interestingly, the M7 sequence was highly conserved between the human and murine protein sequence (FIG. 1A). Among several hybridoma clones with high-affinity binding of the according supernatant to the immobilized peptide M7 in a solid-phase binding assay, clone RC3 (mouse IgG2bκ) showed specific inhibition of Mac-1-CD40L binding, but not of the interaction to other ligands. This antibody clone, subsequently termed anti-M7, bound to a CHO cell line over-expressing native (WT) and permanently activated Mac-1 (del), but not to control CHO cells in western blot (FIG. 1B), confirming successful binding to the target protein.

Moreover, anti-M7 bound to the immobilized peptides M7 (EQLKKSKTL) (SEQ ID NO:9), but not to the control peptides scrambled sM7 (KLSLEKQTK) (SEQ ID NO:12) or the peptide M8 (EEFRIHFT) (SEQ ID NO:13) in a solid phase binding (FIG. 1C), indicating that anti-M7 specifically binds to the immunized peptide. To test binding of anti-M7 to Mac-1 expressing human cells, we coupled the antibody with the fluorochrome Alexa647 and quantified binding to human leukocyte subsets in flow cytometry. Interestingly anti-M7 showed concentration-dependent binding to human leukocytes expressing Mac-1, such as monocytes and neutrophils, but not to lymphocytes as expected (FIG. 1D). Binding of anti-Mac-1 clone M1/70 served as control and showed the same binding properties with highest binding to myeloid cells. These findings demonstrate that the binding sequence M7 within the human Mac-1 I-domain is accessible to binding with the monoclonal antibody anti-M7. Further DNA sequencing revealed CDRs and exact protein sequence of anti-M7 variable regions of heavy and light chain. This is shown in Table 1:

TABLE 1

Protein sequence of anti-M7 variable regions

Light chain
DIQMTQSPSSLSASLGERVSLTCRAS<u>QEISGYL</u>SWHQQKPDGTIKRLLY<u>S
TSTLDSG</u>VPKRFSGSRSGSDYSLTISSLESEDFADYYC<u>LQYAISPPT</u>FGG
GTKLEIK (SEQ ID NO: 1)

Heavy chain
QVTLKESGPGILQTSQTLSLTCSFS<u>GFSLSTSGMG</u>VSWIRQPSGKGLEWL
AH<u>IYWDDDKR</u>YNPSLKSRLTISKDTSRNQVFLKITSVDTTDTATYYC<u>ALN
YYNSTYNFDF</u>WGQGTTLTVSS (SEQ ID NO: 5)

Position of CDR 1,2,3 is underlined

EXAMPLE 3

Specific binding of the antibody anti-M7 to the immobilized peptides M7 (EQLKKSKTL) (SEQ ID NO:9), sM7 (KLSLEKQTK) (SEQ ID NO:12), and M8 (EEFRIHFT) (SEQ ID NO:13) was tested in a solid phase binding with immobilized peptides in 96-well ELISA plates (Nunc). Binding of anti-M7 was detected by addition of biotinylated anti-mouse IgG and subsequent color reaction after incubation with HRP-coupled streptavidin and TMB-substrate. Specific binding was calculated by subtraction of binding of mouse IgG to the peptides. To test binding of the antibody anti-M7 to human leukocytes, anti-M7 was labeled with Alexa Fluor 647 according to the manufacturers protocols (Monoclonal Antibody Labeling Kit, Life Technologies). Human leukocytes were isolated from healthy donors by centrifugation and Red Blood Cell lysis-Leukocytes were stimulated with PMA (200 ng/ml), incubated with anti-M7-Alexa 647 (1 µg and 5 µg) and antibody binding was quantified by flow cytometry.

It was found that anti-M7 is a ligand- and activation specific inhibitor of Mac-1's interaction with CD40L.

To test whether anti-M7 is able to functionally block the interaction of Mac-1 and CD40L, the adhesion of CHO-cells over-expressing a permanently activated Mac-1 mutant (Mac-1-del) to immobilized CD40L was tested in a static adhesion assay. Interestingly, anti-M7 blocked the cell adhesion by 65.6±7.2%, an effect nearly as strong as the anti-human pan-I-Domain blocking reference clone 2LPM19c (inhibition by 92.7±2.0%, FIG. 2A, B). In the experiment a concentration of 10 µg/ml was used. It can be concluded therefrom that in general concentrations of the antibody ranging from 1 to 50 µg/ml and preferably from 5 to 20 µg/ml are used. Most interestingly, in contrast to the reference anti-Mac-1 antibody, anti-M7 did not block adhesion of CHO cells expressing the native, non-activated Mac-1 integrin (FIG. 2C), indicating that blockade by anti-M7 was specific to high-affinity conformation of the integrin. Moreover, inhibition by anti-M7 was not restricted to human proteins, since interaction of murine macrophages and murine CD40L was significantly blocked by anti-M7. Furthermore, blocking by anti-M7 was not unspecifically caused by the $F_c$-fragments of the antibody, since $F_{ab}$-fragment preparations of anti-M7 or anti-Mac-1 were as effective as the whole antibody preparation (FIG. 2D). Different ligands can bind to separate or overlapping binding regions within the Mac-1 I-domain. To test whether anti-M7 is specific for the CD40L binding epitope, a panel of classical Mac-1 ligands, such as Fibrinogen, ICAM-1, NIF, heparin, and RAGE was separately immobilized and binding of Mac-1-del cells was tested in the presence of anti-M7 and anti-Mac-1 (FIG. 2E). Notably, anti-Mac-1 blocked each of the interactions, while blocking capacity of anti-M7 was restricted to CD40L. These data unveil that anti-M7 is an effective and specific inhibitor of the CD40L/Mac-1 interaction.

EXAMPLE 4

Murine peritoneal macrophages were obtained as described above. Flow cytometry revealed that the majority (>90%) of PECs were positive for the macrophage marker F4/80. After overnight starvation macrophages were stimulated with the indicated antibodies against Mac-1 in a concentration of 10 µg/ml for 30 minutes. After the indicated time points, cells were lysed, proteins were separated by SDS-PAGE and blotted to polyvinylidene difluoride membranes. Total protein and the phosphorylated fraction of NFκB, ERK1/2 and p38 were detected by specific antibody binding in western blot (Cell Signaling). The ratio of phosphorylated fractions was calculated and expressed as relative arbitrary unit (AU) normalized to signal of cells stimulated with saline alone.

The test results show that anti-M7 does not induce integrin outside-in signaling, while conventional anti-Mac-1 antibodies induce activation of MAP-kinases and inflammatory cytokine expression in vitro and in vivo.

Conventional anti-Mac-1 antibodies induce activation of the integrin, termed outside-in-signaling mediated by downstream activation of MAP-kinases, such as ERK and p38 upon ligand and antibody binding. It has previously been shown that CD40L is a biased agonist not inducing outside-in signaling events upon binding. To test whether anti-M7 would induce cell activation, thioglycollate-elicited peritoneal macrophages from male, 8 week old C57Bl/6 mice were collected. After overnight starvation in 5% FCS containing RPMI, the macrophages were stimulated with 10 µg/ml of either mouse IgG, anti-human Mac-1 (clone 2LPM19c), anti-mouse Mac-1 (clone M1/70) or anti-M7 for 30 min. Anti-Mac-1 treatment induced phosphorylation of ERK and p38 as quantified by an elevated ratio of the phosphorylated epitopes in western blot (FIG. 3A), while anti-M7 had no effects, indicating that the binding epitope targeted by anti-M7 is not involved in outside-in signaling (FIG. 3B). To assess whether this effect is relevant for an in vivo treatment, Mac-1 antibody clones were injected i.p. in mice and serum concentration of IL-6, TNFα, and MCP-1 were quantified 4 hours after injection. Surprisingly, the Mac-1 reference clone M1/70 (control) strongly elevated cytokine levels, while anti-M7 did not (FIG. 3C). In accordance, levels of pro-inflammatory cytokines increased in in vitro culture of macrophages after antibody stimulation. These findings indicate that anti-M7 is targeting an epitope not causing unwanted outside-in signaling during integrin blockade.

EXAMPLE 5

Before enzymatic digestion, the antibody was dialyzed in a SnakeSkin Dialysis Tubing 10k MWCO against PBS overnight at 4° C. Immobilized papain was used to prepare $F_{ab}$ fragments from anti-M7, anti-Mac-1 (clone M1/70) and an IgG isotype control as indicated according to the manufacturer's instructions (Pierce $F_{ab}$ Preparation Kit, Thermo Scientific). Briefly, $F_{ab}$-fragments were generated in the presence of 25 mM cysteine for 3 h at 37° C., followed by purification on NAb Protein A Spin Columns. Purity of $F_{ab}$-fragments was evaluated on SDS-PAGE.

96-well plates (Nunc) were coated with sCD40L (10 µg/ml) and incubated with CHO-cells expressing constitutively activated Mac-1. Cells were pre-incubated with blocking antibodies (10 µg/mL) as indicated and allowed to adhere for 50 minutes. Adhering cells were counted after repeated washing with PBS. For dynamic adhesion assays, human umbilical endothelial cells (HUVECs) were grown to confluency in 35 mm cell culture dishes, stimulated with TNFα overnight and placed in a parallel flow chamber system (Glycotech). Number of adhering cells was quantified at the indicated shear rate in the presence of the indicated antibodies (10 µg/mL).

For intravital microscopy mice received an intraperitoneal injection of 100 µg of antibodies or 50 µg of $F_{ab}$-fragments i.p. After 15 minutes mice were injected i.p. with 200 ng murine TNFα (R&D Systems). Surgery started 4 hours after TNFα administration. Briefly, mice were anesthetized by intraperitoneal injection of ketamine hydrochloride (Essex) and xylazin (Bayer, Leverkusen, Germany). The mesentery was exteriorized and placed under an upright intravital microscope (AxioVision, Carl Zeiss). Videos of rolling and adhering in mesenteric venules were taken after retro-orbital injection of rhodamine. Rolling leukocyte flux was defined as the number of leukocytes moving at a velocity less than erythrocytes. Adherent leukocytes were defined as cells that remained stationary for at least 30 seconds.

Flow cytometry: Peritoneal exudate cells (PECs) and blood leukocytes were obtained as described below. Remaining red blood cells were removed by incubation with a red blood cell lysing buffer (155 mM NH4Cl, 5.7 mM K2HPO4, 0.1 mM EDTA, pH7.3). Cells were washed in PBS, and Fc-Receptors were blocked by anti-CD16/CD32 (eBioscience) for 10 minutes on ice. Cells were then labeled with the indicated antibodies before quantification with a flow cytometer (FACS Calibur, BD Biosciences). All antibodies were obtained from eBioscience. Distinct leukocyte populations were identified upon cell surface expression of the indicated antigens: granulocytes ($Gr-1^+F4/80^-CD11b^+$ CD115), macrophages ($F4/80^+CD11b^+CD115^-$), inflammatory monocytes ($CD11b^+CD115^+Gr-1^+4/80^-$), non-inflammatory monocytes ($CD11b^+CD115^+Gr-1^-F4/80^-$).

Isolation and cultivation of murine peritoneal macrophages: Antibodies were injected i.p. 30 min before WT mice received an injection of 2 mL of 4% thioglycollate broth (Sigma). A peritoneal lavage was performed after 72 hours. Peritoneal exudate cells (PECs) were quantified and characterized by FACS as described above. In CLP experiments a peritoneal lavage was performed 20 hours after surgery.

It could be shown that treatment with anti-M7 prevents inflammatory leukocyte recruitment in vitro and in vivo and decreases inflammatory cytokine expression.

Mac-1 is a powerful adhesion factor, likely mediating its adhesive function through interaction with different ligands expressed at the endothelium, including ICAM-1, RAGE, and CD40L. To test if anti-M7 blocks cellular adhesion, murine monocyte-like RAW-cells were allowed to adhere on isolated and TNFα-primed murine endothelial cells in vitro in a flow chamber assay. Number of adhering cells decreased after incubation with anti-M7, indicating that CD40L/Mac-1 interaction is required for leukocyte arrest (FIG. 3A). To test for relevance of these findings in vivo, $F_{ab}$-fragment preparation of anti-M7 and an according isotype were injected i.p. prior to intravital microscopy (FIG. 4B). Leukocyte recruitment to inflamed mesenteric venules was monitored after simultaneous stimulation with TNFα for 4 hours to induce inflammatory leukocyte recruitment. Consistently with our in vitro results, we observed that the number of adhering (FIG. 4C), but not of rolling leukocytes (FIG. 4D) was reduced after anti-M7 injection. In accord, leukocyte rolling velocity, displayed as cumulative frequency, was not changed (FIG. 4E), indicating that firm adhesion, but not rolling properties of leukocyte is blocked by anti-M7. To exclude that anti-M7 induces leukocyte depletion we injected anti-M7 or an according isotype control i.p., and quantified leukocyte populations. Of note, no changes were observed in both groups. To test if impaired monocyte arrest would affect down-stream effects, such as transmigration, mice expressing GFP in monocytes (CX3CR1-GFP) were subjected to intravital microscopy in the presence of IgG or anti-M7 $F_{ab}$ preparations after a TNFα challenge for 4 hours (FIG. 4F). In accordance, we observed that anti-M7 treated animals showed lower numbers of monocytes migrated to the perivascular space (FIG. 4G). Finally, we observed that plasma levels of the pro-inflammatory cytokines TNFα, IL-6, and MCP-1 were significantly reduced in mice subjected to intravital microscopy after anti-M7 $F_{ab}$ treatment compared with IgG $F_{ab}$ treated control animals (FIG. 4H). These results clearly indicate that leukocyte adhesion proceeds by the interaction of CD40L and Mac-1 and that this interaction can be functionally blocked by anti-M7 antibody.

EXAMPLE 6

It has also been shown that anti-M7 does not affect venous thrombosis and platelet effector function in vivo.

Mac-1 participates in haemostasis and thrombus formation, presumably by its interaction to the platelet glycoprotein GP1bα. Also, CD40L stabilizes thrombi and its therapeutic inhibition raises thromboembolic complications. To exclude that an antibody according to the invention would induce unwanted thrombus destabilization, venous thrombosis was induced in mesenteric venules of C57Bl/6 mice by ferric chloride. Thrombus formation was visualized by in vivo rhodamine staining in intravital microscopy (FIG. 5A). As described previously, inhibition of Mac-1 by an i.p. injected $F_{ab}$-fragment prolonged vessel occlusion time and increased the release of thrombotic emboli (FIG. 5B, C), confirming that Mac-1 is needed to stabilize thrombi. However, inhibition by anti-M7 did not cause significant changes in vessel occlusion time or release of thrombotic emboli, proposing that participating pathways were not affected. Accordingly, formation of leukocyte-platelet aggregates was diminished by unspecific blockade of Mac-1, but not by specific inhibition of the CD40L/Mac-1 interaction (FIG. 5D). These data propose that anti-M7 is likely not inducing unwanted effects on the haemostatic system.

EXAMPLE 7

Interaction of Mac-1 to CD40L, but not to other ligands, improves skin wound healing. Leukocyte engagement is a critically step in wound healing and delayed wound healing has been reported in Mac-1 null mice. To test whether these effects are mediated by Mac-1's interaction to CD40L, we treated C57Bl/6 mice with i.p.-injections of $F_{ab}$-fragments of either anti-M7, anti-Mac-1 or an according isotype control directly after induction of 4 mm dorsal skin wounds. Interestingly, during the time course of the experiment delayed wound healing in anti-Mac-1 treated mice was not detected. However, skin wounds tent to close faster in Kaplan-Maier wound closure analysis in anti-M7 treated mice and demonstrated a smaller wound surface 6 days after wound induction (FIG. 6A,B). This indicates that specific inhibition of the CD40L/Mac-1 interaction does not affect, but instead seems to exhibit protective effects on skin wound healing.

EXAMPLE 8

Unselective inhibition of Mac-1 aggravates, while specific blockade of its interaction to CD40L improves bacterial clearance, inflammation, and survival during bacterial sepsis.

It has recently been shown that mice with a genetic deficiency of Mac-1 demonstrated decreased survival during bacterial sepsis, highlighting the potential role of the leukocyte integrin in host defense and clearance of bacteria. To elucidate whether ligand-specific blockade of Mac-1 and CD40L is rather beneficial during bacterial sepsis, a model of coecal-ligation and puncture sepsis (CLP) was performed. 20 hours after CLP procedure inflammatory and patrolling monocytes circulating in blood and basic inflammatory parameters were quantified. Interestingly, CLP induced a strong mobilization of inflammatory Gr-1$^+$ monocytes to the circulation, reaching a percentage of the inflammatory subset of about 82.4±4.6% of all monocytes in IgG $F_{ab}$-fragment treated mice. This response was not affected by $F_{ab}$ anti-Mac-1 treatment (77.4±6.0%), but nearly reversed by $F_{ab}$ anti-M7 treatment (56.8±3.7%, FIG. 7A). During CLP, myeloid cells populate the peritoneal cavity. Granulocytes (F4/80$^-$Gr-1$^+$) invading the peritoneal cavity were identified by flow cytometry (FIG. 7B). Both, anti-Mac-1 and anti-M7, strongly reduced granulocyte accumulation by 59.9±12.2% and 73.8±7.1% for anti-Mac-1 and anti-M7, respectively (FIG. 7C). The anti-inflammatory effect of anti-M7 treatment was further reflected by a strong decrease of the acute-phase protein SAA by 63.4±19.7% (FIG. 7D). Notably, anti-M7 improved bacterial clearance in the plasma, while anti-Mac-1 worsened bacterial load in both, plasma and the peritoneal cavity (FIG. 7E). During CLP, accumulation of neutrophils is observed in the periphery, such as the kidney and lung. To quantify granulocyte trafficking to the spleen, ICH was performed against the granulocyte marker Ly6G in kidney sections (FIG. 7F). Notably, both anti-integrin therapies prevented neutrophil accumulation with a stronger effect in anti-Mac-1 treated animals (FIG. 7F). Finally, it was assessed if the new ligand-specific approach according to the invention is beneficial in surviving sepsis. Therefore, CLP was induced and animals were subsequently treated with $F_{ab}$-preparations of IgG, anti-Mac-1 and anti-M7 at 0, 48, and 96 hours after induction of CLP operation.

Survival rate was calculated employing Kaplan-Maier analysis and log-rank testing. Animals treated with anti-Mac-1 showed significantly decreased mean survival compared to IgG-control treated animals (0% vs. 6.7% after 169 hours after CLP-induction for anti-Mac-1 and IgG, respectively). Notably, anti-M7 treated showed a survival rate of 40.0% at the end of the study (FIG. 8), demonstrating that ligand-directed therapy is superior to unspecific inhibition.

EXAMPLE 9

Treatment with anti-M7 improves the infiltration with inflammatory leukocytes in the injured myocardium following myocardial infarction. Accumulation of inflammatory leukocyte occurs after myocardial infarction within days. Inflammatory leukocyte recruited to the infarcted heart cause an inflammatory response that aggravates wound healing and drives heart failure after myocardial infarction. Inhibition of leukocyte infiltration has been proposed to represent a therapeutic strategy, but not such strategy is available. After induction of myocardial infarction in mice by a surgical ligation of the left anterior descending coronary artery (LAD) and treatment with anti-M7 less infiltrating monocytes and neutrophils, a subclass of inflammatory leukocytes that express Mac-1, were found in the injured myocardium. As a result, anti-M7 attenuated heart failure.

---

The invention claimed is:

1. An isolated monoclonal antibody or an antigen-binding portion thereof which
   a) binds to Mac-1,
   b) specifically inhibits the interaction of CD40L with activated Mac-1,
   c) does not bind to non-activated Mac-1, and
   d) does not induce integrin outside-in signaling,
characterized in that it binds specifically to a peptide having the sequence SEQ ID NO: 9 and that it comprises six CDRs selected from the group consisting of SEQ ID NOs:2-4 and SEQ ID NOs:6-8.

2. The isolated monoclonal antibody or antigen-binding portion thereof of claim 1, wherein the monoclonal antibody or an antigen-binding portion thereof limits the expression of inflammatory cytokines.

3. The isolated monoclonal antibody or antigen-binding portion thereof of claim 1, wherein the monoclonal antibody or an antigen-binding portion thereof blocks leukocyte recruitment in vitro and in vivo in intravital microscopy.

4. The isolated monoclonal antibody or antigen-binding portion thereof of claim 1, wherein the monoclonal antibody or an antigen-binding portion thereof does not affect thrombotic and hemostatic functions of Mac-1.

5. The isolated monoclonal antibody or antigen-binding portion thereof of claim 1, wherein the light chain has an identity of at least 80% to the amino acid sequence of SEQ ID NO:1 and that the heavy chain has at least 80% identity to the amino acid sequence of SEQ ID NO:5.

6. The isolated monoclonal antibody or antigen-binding portion thereof of claim 1, wherein the light chain has the amino acid sequence of SEQ ID NO:1.

7. The isolated monoclonal antibody or antigen-binding portion thereof of claim 1, wherein the amino acid sequence of the heavy chain corresponds to SEQ ID NO:5.

8. The isolated monoclonal antibody or antigen-binding portion thereof of claim 1, wherein the monoclonal antibody or an antigen-binding portion thereof is selected from the group comprising $F_{ab}$ fragments, single chain antibodies, diabodies and/or nanobodies.

9. A pharmaceutical composition comprising a pharmaceutically active amount of an antibody or antigen-binding portion thereof of claim 1.

10. The pharmaceutical composition according to claim 9 for the treatment of inflammation.

11. The isolated monoclonal antibody or antigen-binding portion thereof of claim 1, wherein the monoclonal antibodies or antigen-binding portions thereof are humanized.

* * * * *